United States Patent [19]
Kimura et al.

[11] Patent Number: 5,676,938
[45] Date of Patent: Oct. 14, 1997

[54] COSMETIC COMPOSITION

[75] Inventors: Hiroshi Kimura; Yutaka Horie; Yoshiyuki Sato, all of Tokyo, Japan

[73] Assignee: Toshiba Silicone Co., Ltd., Tokyo, Japan

[21] Appl. No.: 462,548

[22] Filed: Jun. 5, 1995

Related U.S. Application Data

[63] Continuation of Ser. No. 143,499, Oct. 15, 1993, abandoned, which is a continuation of Ser. No. 953,140, Sep. 29, 1992, abandoned.

[51] Int. Cl.$^6$ ............................. A61K 7/00; A61K 7/07
[52] U.S. Cl. ......................... 424/78.03; 424/70.12; 424/70.121
[58] Field of Search ................... 424/78.03, 401, 424/70.12, 70.121

[56] References Cited

U.S. PATENT DOCUMENTS

| | | | |
|---|---|---|---|
| 4,915,938 | 4/1990 | Zawadzki | 424/70 |
| 4,988,504 | 11/1991 | Zotto | 424/65 |
| 5,075,103 | 12/1991 | Halloran | 424/71 |
| 5,085,859 | 2/1992 | Halloran | 424/DIG. 2 |
| 5,089,253 | 2/1992 | Halloran | 424/DIG. 2 |
| 5,120,531 | 5/1992 | Wells | 424/70 |
| 5,160,730 | 11/1992 | Dubief | 424/70 |
| 5,173,290 | 12/1992 | Halloran | 424/71 |
| 5,290,545 | 5/1994 | Halloran | 424/71 |

FOREIGN PATENT DOCUMENTS

| | | |
|---|---|---|
| 0417866 | 3/1991 | European Pat. Off. . |
| 3-22989 | 12/1929 | Japan . |
| 48-1503 | 1/1973 | Japan . |
| 48-19487 | 3/1973 | Japan . |
| 61-18708 | 1/1986 | Japan . |
| 61-65808 | 4/1986 | Japan . |
| 61-65809 | 4/1986 | Japan . |
| 61-158910 | 7/1986 | Japan . |
| 61-158913 | 7/1986 | Japan . |
| 61-158914 | 7/1986 | Japan . |
| 61-161209 | 7/1986 | Japan . |
| 61-161211 | 7/1986 | Japan . |
| 61-194009 | 8/1986 | Japan . |
| 62-234012 | 10/1987 | Japan . |
| 62-298511 | 12/1987 | Japan . |
| 62-298512 | 12/1987 | Japan . |
| 62-298518 | 12/1987 | Japan . |
| 62-298519 | 12/1987 | Japan . |
| 63-22010 | 1/1988 | Japan . |
| 63-297313 | 12/1988 | Japan . |
| 63-313710 | 12/1988 | Japan . |
| 63-313713 | 12/1988 | Japan . |
| 2-42008 | 2/1990 | Japan . |
| 2-243612 | 9/1990 | Japan . |
| WO-A8904163 | 5/1989 | WIPO . |

*Primary Examiner*—Sally M. Gardner
*Attorney, Agent, or Firm*—Sughrue, Mion, Zinn, Macpeak & Seas, PLLC

[57] ABSTRACT

A cosmetic composition comprising a silicone resin comprising from 50 to 99 mol % of $R^1Si(O)_{1.5}$ units wherein $R^1$ represents a substituted or unsubstituted monovalent hydrocarbon group and from 1 to 50 mol % of $(R^2)_3Si(O)_{0.5}$ units wherein $R^2$ represents a substituted or unsubstituted monovalent hydrocarbon group, sum of the $R^1Si(O)_{0.5}$ units and the $(R^2)_3Si(O)_{0.5}$ units being 100 mol %.

7 Claims, No Drawings

COSMETIC COMPOSITION

This is a continuation of application Ser. No. 08/143,499 filed on Oct. 15, 1993 (abandoned), which is a continuation of application No. 07/953,140 filed Sep. 29, 1992 (abandoned).

FIELD OF THE INVENTION

The present invention relates to a cosmetic composition. More particularly, this invention relates to a cosmetic composition which has excellent stability and which, after being applied, shows high water repellency, gives a smooth feeling in use, and is less apt to wash off from sweating.

BACKGROUND OF THE INVENTION

The demand for make-up preparations has been diversified steadily in recent years. In response to this, not only have the kinds of make-up preparation products, e.g., lip rouges, foundations, face powders, nail enamels, and so forth, increased, but also each of such preparations is being marketed in various forms including liquid, powder, solid, and emulsion. It should, in particular, be noted that compared to conventional ones, present-day cosmetics have come to be required to have better physical and chemical properties such as water resistance, perspiration resistance (resistance to sebaceous matter), and wear resistance.

In order to satisfy such requirements, the use of a silicone resin having film-forming ability has been proposed. Examples of known applications of film-forming silicone resins to cosmetics include: a make-up cosmetic composition employing a product of hydrolytic condensation of a dichlorosilane and a trichlorosilane for the purpose of imparting water and oil resistance (JP-A-61-18708) (The term "JP-A" as used herein means an "unexamined published Japanese patent application".); a cosmetic composition containing a silicone resin comprising $R_nSiO_{(4-n)/2}$ units and either a volatile hydrocarbon oil or a volatile silicone oil (JP-A-61-158910, JP-A-61-158913, JP-A-61-158914, JP-A-61-161209, and JP-A-61-161211); a hair cosmetic composition containing a silicone resin comprising $R_nSiO_{(4-n)/2}$ units and a high molecular weight silicone oil (JP-A-63-313713); a cosmetic composition containing a mixture of a silicone resin comprising $R\ SiO_{3/2}$ units, $SiO_2$ units, and $R_2SiO$ units and a silicone resin comprising $RSiO_{3/2}$ units and $SiO_2$ units (JP-A-2-42008); a skin cosmetic composition containing a resin comprising $(R)_3SiO_{1/2}$ units and $SiO_2$ units and a volatile silicone oil (JP-A-61-65808 and JP-A-61-65809); a sunscreen cosmetic composition containing a resin comprising $SiO_2$ units, $RSiO_{3/2}$ units, and $R_2SiO$ units and a volatile silicone oil (JP-A-62-234012); a cosmetic composition which contains a silicone resin comprising $R_3SiO_{1/2}$ units and $SiO_2$ units and further comprising $R_2SiO$ units and/or $RSiO_{3/2}$ units and which may also contain a volatile silicone oil or a silicone powder (JP-A-62-298511, JP-A-62-298512, JP-A-62-298518, and JP-A-62-298519); and a hair fixative cosmetic composition comprising a rigid silicone polymer and a volatile carrier (JP-A-63-22010).

Further, applications of cured silicone resin powders to cosmetics are known. Examples thereof include a cosmetic composition containing powder particles of a cured organopolysiloxane (JP-A-61-194009, JP-A-63-313710, and JP-A-2-243612) and a make-up preparation containing truly spherical powder particles of polymethylsilsesquioxane (JP-A-63-297313).

However, these cosmetics have drawbacks. For example, the silicone resins described in JP-A-61-18708 and JP-A-62-234012 are defective in that they have poor stability because molecular weight control is difficult in the production thereof and a large number of reactive functional groups remain in the silicone resins. The silicone resins described in the other JP-A's are defective in that although the amount of reactive functional groups remaining in the silicone resin can be reduced by selecting proper siloxane structural units, it has been still difficult to obtain sufficient stability. In addition, skin preparations employing the silicone resins described in JP-A-61-65808 and JP-A-61-65809 are disadvantageous in, for example, that films formed from the preparations are too sticky and have a poor skin-protective effect. Therefore, improvements in these drawbacks have been desired.

SUMMARY OF THE INVENTION

The present inventors have conducted intensive studies to overcome the problems of the prior art cosmetics. As a result, it has been found that a useful cosmetic composition can be obtained when a silicone resin comprising $R^1SiO_{1.5}$ units and $R^2{}_3SiO_{0.5}$ units (wherein $R^1$ and $R^2$ each represents a substituted or unsubstituted monovalent hydrocarbon group) in a specific proportion is blended, especially when a silicone resin obtained by blocking silanol groups of a silanol group-containing organopolysilsesquioxane comprising $R^1SiO_{1.5}$ units with a triorganosilyl group is blended. The present invention has been completed based on this finding.

Accordingly, an object of the present invention is to provide a cosmetic composition, e.g., a make-up cosmetic composition, skin cosmetic composition, or hair cosmetic composition, which is free from the above-described problems, that is, which after being applied, has sufficient water repellency, lasts long, and gives a good feeling in use.

The cosmetic composition according to the present invention comprises a silicone resin comprising from 50 to 99 mol % of $R^1SiO_{1.5}$ units wherein $R^1$ represents a substituted or unsubstituted monovalent hydrocarbon group and from 1 to 50 mol % of $R^2{}_3SiO_{0.5}$ units wherein $R^2$ represents a substituted or unsubstituted monovalent hydrocarbon group, the sum of the $R^1SiO_{1.5}$ units and $R^2{}_3SiO_{0.5}$ being 100 mol %.

DETAILED DESCRIPTION OF THE INVENTION

Examples of $R^1$ and $R^2$ which are the same or different and each represents a substituted or unsubstituted monovalent hydrocarbon group, include an alkyl group (e.g., methyl, ethyl, propyl, and butyl), an alkenyl group (e.g., vinyl and ally), an aryl group (e.g., phenyl and tolyl), a cycloalkyl group (e.g., cyclohexyl and cyclooctyl), and (groups formed by replacing one or more of the carbon-bonded hydrogen atoms in those groups with a halogen atom, cyano group, amino group, or other substituent (e.g., chloromethyl, 3,3,3-trifluoropropyl, cyanomethyl, γ-aminopropyl, and N-(β-aminoethyl)-γ-aminopropyl). Of these, a methyl group, ethyl group, and phenyl group are preferred from the standpoints of easiness of synthesis and availability of raw materials, and a methyl group, 3,3,3-trifluoropropyl group, and phenyl group are preferred from the standpoint of water repellency.

In the silicone resin used in the present invention, the content of $R^2{}_3SiO_{0.5}$ units should be from 1 to 50 mol % units in all the siloxane units. If the content of $R^2{}_3SiO_{0.5}$ units is below 1 mol %, the effects of the present invention cannot be produced sufficiently. If the content thereof is higher than 50 mol %, such a silicone resin is difficult to synthesize. It is preferable that the silicone resin comprises from 80 to 95 mol % of $R^1SiO_{1.5}$ units and from 5 to 20 mol % of $R^2{}_3SiO_{0.5}$ units.

The silicone resin used in the cosmetic composition of the present invention can be obtained by reacting (A) 100 parts by weight of a silanol group-containing organopolysilsesquioxane comprising $R^1SiO_{1.5}$ units wherein $R^1$ is the same as defined above with (B) from 5 to 100 parts by weight of a silicone compound represented by $(R^2{}_3Si)_aZ$ wherein $R^2$ is the same as defined above, a is an integer of 1 or 2, and when a is 1, Z represents a hydrogen atom, hydroxyl group, or a hydrolyzable group and when a is 2, Z represents —O—, —N(X)—, or —S—, wherein X represents a hydrogen atom, a monovalent hydrocarbon group having from 1 to 4 carbon atoms, or $R^2{}_3Si$—.

Examples of the hydrolyzable group of Z include an alkoxy group (e.g., methoxy, ethoxy, propoxy, isopropoxy, and butoxy), an alkenyloxy group (e.g., propenoxy), an acyloxy group (e.g., acetoxy and benzoxy), an organooxime group (e.g., acetone oxime and butanone oxime), an organoaminoxy group (e.g., dimethylaminoxy and diethylaminoxy), an organoamino group (e.g., dimethylamino, diethylamino, and cyclohexylamino), and an organoamido group (e.g., N-methylacetamido). Of these, the alkoxy groups, especially methoxy and ethoxy, are preferred from the standpoints of availability of raw materials and easiness of reaction control.

The polysilsesquioxane, ingredient (A), can be synthesized by a conventional method. For example, it may be obtained by hydrolytic condensation of an organotrichlorosilane or an organotrialkoxysilane using excess water. In such reactions, polysilsesquioxanes having various degrees of polymerization can be obtained by changing or controlling the amount of water, kind of hydrolysis catalyst, time and temperature for the condensation reaction, and other factors. The polysilsesquioxanes thus obtained generally contain silanol groups, and a lower silanol group content can be attained by increasing the degree of polymerization of the polymer.

Since the silicone resin used in the cosmetic composition of the present invention preferably is solid at room temperature and contains no or only a slight amount of volatile matter, it is preferred that the silanol group-containing organopolysilsesquioxane used to produce the silicone resin has a molecular weight of 1,000 or more. From the standpoint of obtaining a silicone resin which is solid and non-sticky at room temperature, it is especially preferable that the molecular weight of the organopolysilsesquioxane is 6,000 or more. From the standpoint of obtaining a silicone resin having good thermoplasticity, it is preferable that the molecular weight of the organopolysilsesquioxane is 20,000 or less, more preferably 15,000 or less.

Such polysilsesquioxanes, in general, have silanol group contents of from 1 to 10% by weight. In the present invention, however, it is preferred to use a polysilsesquioxane having a silanol group content of from 1 to 5% by weight.

Most of such polysilsesquioxanes are a liquid or solid having a thermoplastic property at room temperature and can heat-cure upon long-term heating at high temperatures. Of these, a polysilsesquioxane having a softening point of from 10° to 300° C. is preferred in that it can produce a silicone resin which shows good properties when used in cosmetic compositions.

The silicone compound, ingredient (B), represented by $R^2{}_3Si)_aZ$ functions to silylate silanol groups of ingredient (A). Specific examples of ingredient (B) include hydrogensilanes such as trimethylsilane and triethylsilane; chlorosilanes such as trimethylchlorosilane, triethylchlorosilane, triphenylchlorosilane, and $CF_3(CH_2)_2Si(CH_3)_2Cl$; silanols such as trimethylsilanol; alkoxysilanes such as trimethylmethoxysilane, trimethylethoxysilane,

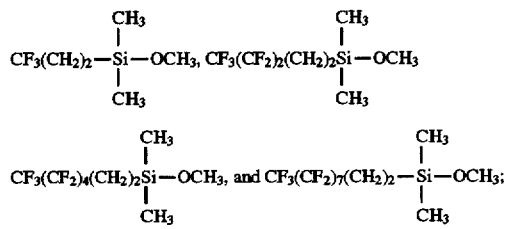

aminosilanes such as $(CH_3)_3SiNHCH_3$, $(CH_3)_3SiNHC_2H_5$, $(CH_3)_3SiN(CH_3)_2$, and $(CH_3)_3SiN(C_2H_5)_2$; acyloxysilanes such as $(CH_3)_3SiOCOCH_3$; and silazanes such as hexamethyldisilazane, 1,3-divinyltetramethyldisilazane,

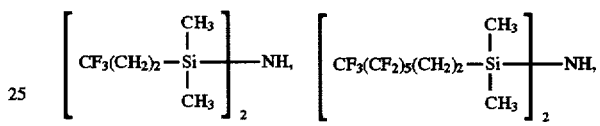

and $[(CH_3)_3Si]_3N$.

Of these, silazanes and chlorosilanes are preferred from the standpoint that reaction control and removal of unreacted raw materials are easy.

The reaction of ingredient (A) with ingredient (B) can be carried out according to a conventional method for the silylation of silanols. For example, where ingredient (B) is a silazane or a chlorosilane, the reaction easily proceeds by merely mixing ingredient (A) and ingredient (B) and heating the mixture.

The amount of ingredient (B) used preferably is from 5 to 100 parts by weight per 100 parts by weight of ingredient (A). If the amount of ingredient (B) is below 5 parts by weight, sufficient silylation cannot be conducted, so that the reaction mixture may gel during reaction or the thus-obtained silicone resin may have poor thermal stability. An amount of ingredient (B) larger than 100 parts by weight is not preferred in that not only does a considerable part of the ingredient (B) remain unreacted which is economically disadvantageous, but also it requires much time to remove the unreacted part of ingredient (B).

It is preferable that the silylation reaction described above is conducted in an organic solvent in order to regulate reaction temperature and to control a condensation reaction which may take place as a side reaction. Examples of the organic solvent include hydrocarbon solvents such as toluene, xylene, hexane, industrial gasolines, mineral spirits, and kerosene, ether solvents such as tetrahydrofuran and dioxane, and chlorinated hydrocarbon solvents such as dichloromethane and dichloroethane.

The temperature for the silylation reaction is not particularly limited, but it is preferred to arbitrarily determine the temperature in the range of from room temperature to 200° C.

By-products, such as hydrochloric acid, ammonia, ammonium chloride, and alcohols, resulting from the silylation reaction can be removed by washing with water or removed by evaporation simultaneously with the solvent.

The silicone resin obtained by the method described above is generally a thermoplastic resin having a softening point of from 5° to 300° C. It is preferred that the silicone resin to be blended with the cosmetic composition of the present invention has a softening point of 50° C. or more because use of such a silicone resin enables the preparation to show non-stickiness. For use as such a silicone resin, two or more silicone resins having different softening points may be blended in a proportion such that the resins have a softening point of 50° C. or more. From the standpoint of obtaining a cosmetic composition showing good luster, a silicone resin having a softening point of 200° C. or less is preferred. An especially preferred range of the softening point of the silicone resin for use in the cosmetic composition of the present invention is from 80° to 150° C.

The silicone resin used in the present invention is characterized in that due to the silylation of silanol groups, the amount of silanol groups remaining in the silicone resin is as small as 0.5% by weight or less. Because of such a low silanol group content, the silicone resin does not cure even upon long-term heating or the like and shows good stability. It is preferable for the silicone resin used in the present invention to have a silanol group content of from 0.01 to 0.3% by weight because such a silicone resin can impart good properties to the cosmetic composition.

The molecular weight of a silicone resin to be produced is determined by the molecular weight of the polysilsesquioxane, ingredient (A), as a raw material therefor, the amount of silanol groups to be silylated, the kind of ingredient (B) as a silylating agent, and the like. A preferred range of the molecular weight of the silicone resin is almost the same as that for ingredient (A). Specifically, the preferred range thereof is from 1,000 to 20,000, more preferably from 6,000 to 15,000, because such a silicone resin can impart good properties to the cosmetic composition of the present invention.

The silicone resin used in the present invention is a liquid or a solid having thermoplasticity. This resin is soluble in organic solvents and can be emulsified with an emulsifying agent or the like. Therefore, this silicone resin is different from cured silicone resins which do not have thermoplasticity and are insoluble in solvents and which are generally known as silicone resin powders.

As described above, the silicone resin used in the present invention is obtained by synthesizing a polysilsesquioxane by polymerization of, for example, the organotrichlorosilane or organotrialkoxysilane, and then silylating silanol groups of the resulting polymer with ingredient (B), and is characterized by having both a preferred degree of polymerization and a low silanol group content. If the starting material for ingredient (A) (e.g., organotrichlorosilane or organotrialkoxysilane) and ingredient (B) are subjected to hydrolytic co-condensation to obtain a conventional silicone resin, the thus-obtained silicone resin has a high silanol group content and a silicone resin having a low silanol group-content like the silicone resin as used in the present invention cannot be obtained. Although such a high silanol group content may be decreased by conducting a condensation reaction by heating or the like, the resin is cured by the treatment. Hence, it is difficult to obtain, by such a method, a silicone resin having thermoplasticity and stability to heating, such as the silicone resin used in the present invention.

By blending the thus-obtained silicone resin with other ingredients described below in an amount of from 0.1 to 99% by weight based on the weight of the cosmetic composition, a cosmetic composition can be obtained such as a make-up cosmetic composition, e.g., a foundation, pressed powder, eyeshadow, nail enamel, or lipstick, a skin cosmetic composition, a hair cosmetic composition, or other cosmetic compositions.

Raw materials conventionally used for cosmetics may be suitably selected according to the kind of the cosmetic composition of the present invention and blended therewith in addition to the above-described silicone resin as an essential component.

Examples of such raw materials include oily materials such as various kinds of hydrocarbons, higher fatty acids, oils and fats, esters, higher alcohols, waxes, and silicone oils, e.g., squalane, liquid paraffins, isoparaffins, vaseline, microcrystalline waxes, ozokerite, ceresin, myristic acid, palmitic acid, stearic acid, oleic acid, isostearic acid, cetyl alcohol, stearyl alcohol, hexadecyl alcohol, oleyl alcohol, cetyl 2-ethylhexanoate, 2-ethylhexyl palmitate, 2-octyldodecyl myristate, 2-octyldodecyl gum esters, neopentyl glycol 2-ethylhexanoate, isooctylic acid triglyceride, 2-octyldodecyl oleate, isopropyl myristate, isopropyl palmitate, isostearic acid triglyceride, coconut oil fatty acid triglyceride, olive oil, avocado oil, bees wax, myristyl myristate, mink oil, and lanolin; organic solvents such as acetone, toluene, butyl acetate, and ethyl acetate; resins such as alkyd resins, acrylic resins, and urea resins; plasticizers such as camphor and acetyl tributyl citrate; and other ingredients such as ultraviolet absorbers, antioxidants, antiseptics, surfactants, humectants, perfumes, water, alcohols, and thickeners.

Powdery materials may be added to the cosmetic composition of the present invention. Examples thereof include inorganic powders such as powders of talc, kaolin, sericite, common mica, synthetic mica, phlogopite, lepidolite, biotite, lithia mica, vermiculite, magnesium carbonate, calcium carbonate, diatomaceous earth, magnesium silicate, calcium silicate, aluminum silicate, barium silicate, barium sulfate, strontium silicate, metal salts of tungstic acid, silica, hydroxyapatite, zeolite, boron nitride, and ceramics; organic powders such as nylon powder, polyethylene powder, benzoguanamine powder, polytetrafluoroethylene powder, distyrene-benzene pinhole polymer powder, and fine crystals of cellulose; silicone powders such as powders of silicone rubbers and silicone resins; inorganic white pigments such as titanium oxide and zinc oxide; inorganic red pigments such as iron oxide (red iron oxide) and iron titanate; inorganic brown pigments such as γ-iron oxide; inorganic yellow pigments such as yellow iron oxide and loess; inorganic black pigments such as black iron oxide and carbon black; inorganic violet pigments such as manganese violet and cobalt violet; inorganic green pigments such as chromium oxide, chromium hydroxide, and cobalt titanate; inorganic blue pigments such as ultramarine and Prussian blue; pearlescent pigments such as titanium oxide-coated mica, titanium oxide-coated bismuth oxychloride, bismuth oxychloride, titanium oxide-coated talc, pearl essence, and colored titanium oxide-coated mica; metal powder pigments such as aluminum powder and copper powder; organic pigments such as Red No.201, Red No.202, Red No.204, Red No.205, Red No.220, Red No.226, Red No.228, Red No.405, Orange No.203, Orange No.204, Yellow No.205, Yellow No.401, and Blue No.404; other organic pigments such as zirconium, barium, or aluminum lakes of Red No.3, Red No.104, Red No.106, Red No.227, Red No.203, Red No.401, Red No.505, Orange No.205, Yellow No.4, Yellow No.5, Yellow No.202, Yellow No.203, Green No.3, and Blue No.1; and natural dyes such as chlorophyll and β-carotene. Powdery materials that can be added to the cosmetic composition of the present invention are not limited to these examples.

The cosmetic composition of the present invention spreads well and, after being applied to the skin, gives a nonsticky and dry feeling, does not wash off from sweating or the like, and is less apt to be washed off by washing with water or the like. Thus, the cosmetic composition has good properties. In addition, the cosmetic composition of the present invention shows good stability over a long period of time. Where the cosmetic composition according to the present invention is a hair cosmetic composition, it imparts softness, a nonsticky and dry feeling, ease of combing, and good luster to the hair and shows good hair-setting properties and high moisture resistance due to excellent water repellency. Where the cosmetic composition of the present invention is a skin cosmetic composition, it gives a nonsticky and dry feeling and shows good water resistance due to excellent water repellency. Further, in the case of a make-up cosmetic composition, it spreads well and evenly, lasts long due to excellent water repellency and water resistance, and gives luster, good appearance depending on the coloring properties of the pigments employed, and good slip properties.

The present invention will be explained in more detail by reference to the following examples, but the invention is not construed as being limited thereto. In the Synthesis Examples, Examples, and Comparative Examples, all parts and percents are by weight and the viscosity values are measured at 25° C.

PREPARATION EXAMPLE 1

Into a flask were introduced 220 parts (1 mol) of methyltriisopropoxysilane and 150 parts of toluene. 108 Parts of hydrochloric acid having a hydrogen chloride concentration of 1% was added thereto dropwise over a period of 20 minutes with stirring to hydrolyze the silane. 40 Minutes after the dropwise addition, the stirring was stopped and the reaction mixture was separated into an aqueous phase and an organic phase. The organic phase was separated from the aqueous phase and washed with water to remove the hydrochloric acid. Further, the toluene was removed under a reduced pressure, thereby preparing a methylpolysilsesquioxane, P-1, having a molecular weight of 12,000, softening point of 115° C., and silanol group content of 1.2%. Into a flask were then introduced 100 parts of the thus-prepared polysilsesquioxane, 200 parts of toluene, 10 parts of trimethylchlorosilane, and 50 parts of hexamethyldisilazane. The resulting mixture was stirred for 2 hours with heating at the reflux temperature of the toluene. By-products of the reaction, i.e., ammonia and hydrochloric acid or salts thereof, were removed from the reaction mixture by water-washing, and the toluene was removed by evaporation under a reduced pressure. Thus, a trimethylsilyl-substituted silicone resin, A-1, having a softening point of 80° C. was obtained. This silicone resin A-1 had a silanol group content of 0.3%.

In this preparation example and other preparation examples described hereinafter, softening points were measured in accordance with the ring-and-ball softening point method as provided for in JIS C 2104. Molecular weights were measured using a gel permeation chromatograph (HLC-802U, manufactured by Tosoh Corp., Japan) and calculated for standard polystyrene. In this example, the molecular weight of the methylpolysilsesquioxane and that of the silylated silicone resin were found to be almost the same. Further, the silanol group content of a silicone resin was determined by heating the resin at 300° C. for 2 hours, measuring the amount of water generated during the two-hour heating by means of a coulometric water meter, Type CA-06 (manufactured by Mitsubishi Kasei Corporation, Japan), and then calculating the silanol group content using the following equation.

$$\text{Silanol group content (\%)} = \frac{(\text{Amount of water generated}) \times 34/18}{\text{Weight of the silicone resin}} \times 100$$

PREPARATION EXAMPLE 2

The same procedures as in Preparation Example 1 were conducted except that hydrochloric acid having a hydrogen chloride concentration of 0.5% was used in place of the hydrochloric acid used in Preparation Example 1. As a result, a methylpolysilsesquioxane, P-2, having a molecular weight of 2,000, softening point of 45° C., and silanol group content of 4.5% and a trimethylsilylsubstituted silicone resin, A-2, having a softening point of 10° C. were obtained. This silicone resin A-2 had a silanol group content of 0.4%.

PREPARATION EXAMPLE 3

Methylpolysilsesquioxane P-1 was treated in the same manner as in Preparation Example 1 except that 3,3,3-trifluoropropyldimethylchlorosilane and bis(3,3,3-trifluoropropyl)tetramethyldisilazane were used in place of trimethylchlorosilane and hexamethyldisilazane, respectively. As a result, a silylated silicone resin, A-3, having a softening point of 85° C. was obtained. This silicone resin A-3 had a silanol group content of 0.3%.

PREPARATION EXAMPLE 4

The same procedures as in Preparation Example 1 were conducted except that 110 parts (0.5 mol) of methyltriisopropoxysilane and 105.8 parts (0.5 mol) of phenyltrichlorosilane were used in place of 220 parts (1.0 mol) of methyltriisopropoxysilane and water was used in place of hydrochloric acid having a hydrogen chloride concentration of 1%. As a result, an organopolysilsesquioxane, P-3, having a molecular weight of 13,000, softening point of 130° C., and silanol group content of 2.5% and a trimethylsilyl-substituted silicone resin, A-4, having a softening point of 95° C. were obtained. This silicone resin A-4 had a silanol group content of 0.4%.

PREPARATION EXAMPLE 5

The same procedures as in Preparation Example 1 were conducted except that 176 parts (0.8 mol) of methyltriisopropoxysilane and 46.3 parts (0.2 mol) of 3,3,3-trifluoropropyltrichlorosilane were used in place of 220 parts (1.0 mol) of methyltriisopropoxysilane and water was used in place of hydrochloric acid having a hydrogen chloride concentration of 1%. As a result, an organopolysilsesquioxane, P-4, having a molecular weight of 8,000, softening point of 105° C., and silanol group content of 2.0% and a trimethylsilyl-substituted silicone resin, A-5, having a softening point of 71° C. were obtained. This silicone resin A-5 had a silanol group content of 0.3%.

PREPARATION EXAMPLE 6 (COMPARATIVE)

The same procedures for preparing polysilsesquioxane P-1 in Preparation Example 1 were conducted except that co-hydrolysis was performed using 166.4 parts (0.8 mol) of tetraethoxysilane and 20.8 parts (0.2 mol) of trimethylmethoxysilane in place of the hydrolysis of 220 parts (1.0 mol) of methyltriisopropoxysilane. As a result, a silicone resin, B-1, having a molecular weight of 2,000 and a silanol group content of 4.5% was obtained as a comparative resin.

PREPARATION EXAMPLE 7 (COMPARATIVE)

The same procedures for preparing polysilsesquioxane P-1 in Preparation Example 1 were conducted except that co-hydrolysis was performed using 66 parts (0.3 mol) of methyltriisopropoxysilane, 41.6 parts (0.4 mol) of trimethylmethoxysilane, and 36 parts (0.3 mol) of dimethyldimethoxysilane in place of the hydrolysis of 220 parts (1.0 mol) of methyltriisopropoxysilane. As a result, a silicone resin, B-2, having a molecular weight of 3,000 and a silanol group content of 3.0% was obtained as a comparative resin.

The silicone resins obtained in Preparation Examples 1, 4, 6, and 7 were evaluated for stability by the following method.

[Stability of Silicone Resins]

Evaluation Method

Each of the silicone resins was dissolved in isopropyl alcohol at a concentration of 20% and this solution was allowed to stand at room temperature for one month. Whether each solution underwent a change in appearance or viscosity through the standing was examined. The results obtained are shown in Table 1.

TABLE 1

| | Silicone resin | | | | | |
|---|---|---|---|---|---|---|
| | A-1 | A-4 | P-1 | P-3 | B-1 | B-2 |
| Initial appearance | Colorless and clear | | | | | |
| Appearance change | No change | | | Turned milky | | |
| Viscosity change | No change | | | Increased | | |

Hair cosmetic compositions, skin cosmetic compositions, make-up cosmetic compositions, and the like were formulated using the silicone resins prepared above, and these cosmetic compositions were evaluated.

[Hair Cosmetic Compositions]

Evaluation Method

Curl Retention: A standard hair sample having a length of 15 cm was curled using a curler in a manner such that the curled hair has a length of about 8 cm. In this curling, the hair sample was wound on the curler, with a hair fixative composition being applied thereto, and the hair sample was revolved on the curler at 25 rpm so that the hair cosmetic composition was surely dispersed uniformly throughout the hair sample. Thereafter, the thus-curled hair sample was hung from a peg in a cabinet having a temperature of 24° C. and a relative humidity of 90%, and allowed to stand for 3 hours. The length of the resulting hair sample was measured and the curl retention was calculated using the following equation.

$$\text{Curl retention (\%)} = \frac{\text{Hair length just after curling}}{\text{Hair length after standing}} \times 100$$

Moisture Absorption: Hair samples coated with a hair fixative composition were allowed to stand for 3 hours in atmospheres having relative humidities of 40%, 60%, and 80%, and the amount of water (%) absorbed by each hair sample during the standing was measured.

Feelings by Sensual Test: Softness, ease of combing, nonstickiness, and shine were evaluated based on the criteria shown in Table 2 below.

TABLE 2

| | Softness | Ease of Combing | Nonstickiness | Shine |
|---|---|---|---|---|
| ⊚: | Very soft | Excellent | Nonsticky | Excellent |
| ○: | Soft | Good | Very slightly sticky | Good |
| △: | Slightly stiff | Slightly poor | Slightly sticky | Same as untreated hair |
| ×: | Stiff | Poor | Sticky | Decreased shine |

EXAMPLES 1 TO 3 AND COMPARATIVE EXAMPLES 1 TO 3

(Hair Fixative)

According to the formulations shown in Table 3, hair fixative compositions were formulated. These compositions were evaluated by the method described above, and the results obtained are shown in Table 4.

TABLE 3

| | Example | | | Comparative Example | | |
|---|---|---|---|---|---|---|
| Components (parts) | 1 | 2 | 3 | 1 | 2 | 3 |
| Silicone resin A-1 | 2.0 | 1.8 | 1.9 | | | |
| Silicone resin A-2 | | 0.2 | | | | |
| Silicone resin B-1 | | | | | | 2.0 |
| Dimethylpolysiloxane (viscosity 1,000,000 cP) | | | 0.1 | | | |
| Poly(methyl methacrylate) | | | | 2.0 | | |
| Polysilsesquioxane P-1 | | | | | 1.8 | |
| Polysilsesquioxane P-2 | | | | | 0.2 | |
| Ethanol | 23 | 20 | 20 | 20 | 20 | 20 |
| Octamethylcyclotetrasiloxane | 15 | 18 | 18 | 18 | is | 18 |
| Trichlorofluoromethane/dichlorofluoromethane (60/40) | 60 | 60 | 60 | 60 | 60 | 60 |

TABLE 4

| | Example | | | Comparative Example | | |
|---|---|---|---|---|---|---|
| | 1 | 2 | 3 | 1 | 2 | 3 |
| Curl retention (%) | 91 | 92 | 93 | 70 | 71 | 89 |
| Moisture absorption (%) | | | | | | |
| Relative humidity | | | | | | |
| 40% | 0.5 | 0.6 | 0.7 | 0.2 | 1.4 | 1.4 |
| 60% | 1.0 | 1.1 | 1.2 | 1.2 | 1.7 | 1.8 |
| 80% | 2.2 | 2.5 | 2.7 | 10.1 | 3.8 | 4.0 |
| Feelings | | | | | | |
| Softness | ○ | ○ | ○ | × | ○ | ○ |
| Ease of combing | ○ | ○ | ○ | △ | △ | △ |
| Nonstickiness | ⊚ | ⊚ | ⊚ | ○ | △ | △ |
| Shine | ○ | ○ | ⊚ | △ | ○ | ○ |

EXAMPLE 4

(Rinse-in-Shampoo)

15.0 Parts of betaine lauramidopropyldimethylaminoacetate, 7.0 parts of sodium poly(oxyethylene) lauryl ether sulfate, 0.5 part of poly(oxyethylene) distearate, 0.3 part of cationic cellulose, 3.0 parts of glycerin, and 0.2 part of methylparaben were mixed by stirring at 80° C. 68.0 Parts of purified water was added thereto and this mixture was cooled to 50° C. with stirring. Thereto was then added a dispersion prepared beforehand by mixing 2.0 parts of silicone resin A-1, 1.0 part of dimethylpolysiloxane having a viscosity of 1,000,000 cP, and 3.0 parts of octamethylcyclotetrasiloxane. The resulting mixture was homogenized and cooled to 40° C., thereby obtaining a rinse-in-shampoo. This shampoo was actually used and then evaluated for the feelings described above. The results obtained are shown in Table 5.

EXAMPLE 5

A rinse-in-shampoo was obtained in the same manner as in Example 4 except that 2.0 parts of silicone resin A-4, 1.0 part of a methyl phenyl silicone oil having a degree of polymerization of 2,000, and 3.0 parts of tetrakis(3,3,3-trifluoropropyl)tetramethylcyclotetrasiloxane were used in place of silicone resin A-1, dimethylpolysiloxane, and octamethylcyclotetrasiloxane. This shampoo was actually used and then evaluated for the feelings described above. The results obtained are shown in Table 5.

COMPARATIVE EXAMPLE 4

A rinse-in-shampoo was obtained in the same manner as in Example 4 except that silicone resin B-1 was used in place of silicone resin A-1. This shampoo was actually used and then evaluated for the feelings described above. The results obtained are shown in Table 5.

COMPARATIVE EXAMPLE 5

A rinse-in-shampoo was obtained in the same manner as in Example 4 except that silicone resin B-2 was used in place of silicone resin A-1. This shampoo was actually used and then evaluated for the feelings described above. The results obtained are shown in Table 5.

EXAMPLE 6

(Hair Conditioner)

1.0 Part of ethylene glycol distearate, 10.0 parts of liquid paraffin, 5.0 parts of squalane, 1.5 parts of stearyl alcohol, 3.0 parts of polydimethylsiloxane (viscosity; 20 cP), 6.0 parts of stearic acid, 4.5 parts of poly(oxyethylene) stearyl ether, 2.0 parts of poly(oxyethylene) cetyl ether, and 1.5 parts of silicone resin A-1 were mixed by stirring at 80° C. Thereto was added a dispersion prepared beforehand by mixing 6.0 parts of 1,3-butylene glycol, 0.1 part of methylparaben, and 59.4 parts of purified water. The resulting mixture was cooled to 35° C. with stirring, thereby obtaining a hair conditioner. This hair conditioner was actually used and then evaluated for the feelings described above. The results obtained are shown in Table 5.

COMPARATIVE EXAMPLE 6

A hair conditioner was obtained in the same manner as in Example 6 except that silicone resin B-2 was used in place of silicone resin A-1. This hair conditioner was actually used and then evaluated for the feelings described above. The results obtained are shown in Table 5.

TABLE 5

| Feelings | Example |  |  | Comparative Example |  |  |
|---|---|---|---|---|---|---|
|  | 4 | 5 | 6 | 4 | 5 | 6 |
| Softness | ⊙ | ⊙ | ⊙ | Δ | Δ | ○ |
| Ease of combing | ○ | ⊙ | ⊙ | Δ | Δ | Δ |
| Nonstickiness | ⊙ | ⊙ | ⊙ | Δ | Δ | Δ |
| Shine | ○ | ○ | ⊙ | ○ | ○ | ○ |

[Skin Cosmetic Compositions]

Evaluation Method

Skin cosmetic compositions to be evaluated were subjected to a sensual test in which five panelists actually used the compositions and evaluated the feeling thereof.

○: Nonsticky and dry feeling
Δ: Slightly sticky feeling
x: Sticky feeling with poor water repellency

EXAMPLE 7

(Hand Moisturizer Lotion)

60 Parts of silicone resin A-1 prepared in Preparation Example 1 was mixed with 20 parts of octamethylcyclotetrasiloxane and 20 parts of decamethylcyclopentasiloxane and dissolved therein by heating the mixture to 50° C. To this solution were added 3 parts of poly(oxyethylene(13)) octylphenyl ether and 3 parts of poly(oxyethylene(3)) octylphenyl ether. This mixture was heated to 80° C. to obtain a uniform solution. Thereto was added a uniform liquid mixture of 30 parts of water, 2 parts of propylene glycol, and 2 parts of dipropylene glycol. The resulting mixture was emulsified using a homogenizer, thereby obtaining a hand moisturizer lotion. This lotion was evaluated for use feeling by the above-described method. The results obtained are shown in Table 6.

COMPARATIVE EXAMPLE 7

A hand moisturizer lotion was obtained in the same manner as in Example 7 except that the amounts of octamethylcyclotetrasiloxane and decamethylcyclopentasiloxane were changed to 45 parts and 35 parts, respectively, and 20 parts of dimethylpolysiloxane (I) (degree of polymerization: 5,000) was used in place of silicone resin A-1. This lotion was evaluated for use feeling by the above-described method. The results obtained are shown in Table 6.

EXAMPLE 8

(Hand Lotion)

A mixture having the composition shown below was heated to dissolve the soluble ingredients, thereby obtaining a hand lotion. This lotion was evaluated for use feeling by the above-described method. The results obtained are shown in Table 6.

| Composition: |  |
|---|---|
| Octamethyltrisiloxane | 60.0 parts |
| Decamethylcyclopentasiloxane | 34.0 parts |
| Silicone resin A-1 | 4.5 parts |
| Silicone resin A-2 | 1.3 parts |
| Dimethylpolysiloxane (II)*[1] | 0.2 part |

*[1]Degree of polymerization 7,000

COMPARATIVE EXAMPLE 8

A hand lotion was obtained in the same manner as in Example 8 except that 4.5 parts of dimethylpolysiloxane (III) having a degree of polymerization of 500 was used in place of silicone resins A-1 and A-2 and the amount of dimethylpolysiloxane (II) was changed from 0.2 part to 1.5 parts. This lotion was evaluated for use feeling by the above-described method. The results obtained are shown in Table 6.

EXAMPLE 9

(Hand Cream)

A mixture having the composition shown below was heated to 70°–80° C. to dissolve the soluble ingredients. Further, the undissolved ingredients were sufficiently dispersed with a homomixer, thereby obtaining a hand cream. This cream was evaluated for use feeling by the above-described method. The results obtained are shown in Table 6.

| Composition: | |
|---|---|
| Microcrystalline wax | 3.0 parts |
| Solid paraffin | 2.0 parts |
| Bees wax | 3.0 parts |
| Reduced lanolin | 5.0 parts |
| Liquid pardffin | 15.0 parts |
| Spherical methylpolysilsesquioxane-resin fine particles*hu 2 | 5.0 parts |
| Silicone resin A-5 | 45.0 parts |
| Methyl phenyl silicone oil*³ | 2.0 parts |
| Octamethylcyclotetrasiloxane | 20.0 parts |

*²Average particle diameter 0.5 μm
*³Degree of polymerization 2,000

COMPARATIVE EXAMPLE 9

A hand cream was obtained in the same manner as in Example 9 except that silicone resin B-1 was used in place of silicone resin A-5. This cream was evaluated for use feeling by the above-described method. The results obtained are shown in Table 6.

EXAMPLE 10

(Sunscreen Cream)

28.0 Parts of octamethylcyclotetrasiloxane, 8.0 parts of silicone resin A-1, 5.0 parts of liquid paraffin, 1.5 parts of octyl p-methoxycinnamate, 6.0 parts of a polyether-modified silicone (viscosity: 400 cP, poly(oxyethylene) group content: 20%), and 0.2 part of a perfume were mixed. This mixture was heated to dissolve the soluble ingredients and held at 70° C., thereby obtaining an oil phase part. On the other hand, 43.1 parts of water, 3.0parts of sodium L-glutamate, 5.0 parts of 1,3-butylene glycol, and 0.2 part of an antiseptic were mixed, and this mixture was heated to dissolve the soluble ingredients. The resulting solution was held at 70° C. to obtain an aqueous phase part. This aqueous phase part was added to the above-prepared oil phase part. The resulting mixture was sufficiently agitated with an emulsifier to obtain an emulsion, which was then cooled with stirring. After the emulsion had cooled to 35° C. or less, it was poured into a container and then allowed to stand to cool and solidify, thereby obtaining a sunscreen cream. This cream was evaluated for use feeling by the above-described method. The results obtained are shown in Table 6.

COMPARATIVE EXAMPLE 10

A sunscreen cream was obtained in the same manner as in Example 10 except that silicone resin B-2 was used in place of silicone resin A-1. This cream was evaluated for use feeling by the above-described method. The results obtained are shown in Table 6.

TABLE 6

| | Example | | | | Comparative Example | | | |
|---|---|---|---|---|---|---|---|---|
| | 7 | 8 | 9 | 10 | 7 | 8 | 9 | 10 |
| Panelist 1 | ○ | ○ | ○ | ○ | x | x | Δ | Δ |
| Panelist 2 | ○ | ○ | ○ | ○ | x | x | Δ | Δ |
| Panelist 3 | ○ | ○ | ○ | ○ | x | x | Δ | Δ |
| Panelist 4 | ○ | ○ | ○ | ○ | x | x | Δ | Δ |
| Panelist 5 | ○ | ○ | ○ | ○ | x | x | Δ | Δ |

The lotion of Example 7 gave a pleasant moist feeling. The lotion of Example 8 and the cream of Example 9 showed good water repellency even after washing with a soap.

[Make-up Cosmetic Compositions]

Evaluation Method

Make-up cosmetic compositions to be evaluated were subjected to a sensual test in which ten panelists actually used the compositions and evaluated for use feelings (spreadability, long-lasting property, appearance, and slip property) based on the criteria shown below. The results obtained for each item are shown as the average of evaluation ratings by the ten panelists.

○: Excellent

Δ: Good x: Ordinary

EXAMPLE 11

(Oil-Based Foundation)

4 Parts of microcrystalline wax, 1 part of sorbitan sesquioleate, 4 parts of liquid paraffin, 2 parts of lanolin alcohol, 25 parts of octamethylcyclotetrasiloxane, 10 parts of decamethylcyclopentasiloxane, and 6 parts of silicone resin A-5 prepared in Preparation Example 5 were mixed, and this mixture was heated to 70°–80° C. to dissolve the soluble ingredients. Thereto were added 2 parts of yellow iron oxide, 15 parts of titanium oxide, 1 part of red iron oxide, 5 parts of talc, and 25 parts of kaolin. The resulting mixture was stirred to uniformly disperse these particulate ingredients and then cooled while being degassed, thereby obtaining an oil-based foundation. This foundation was evaluated for use feelings by the above-described method. The results obtained are shown in Table 7.

COMPARATIVE EXAMPLE 11

An oil-based foundation was obtained in the same manner as in Example 11 except that 6 parts of dimethylpolysiloxane having a viscosity of 100,000 cP was used in place of silicone resin A-5. This foundation was evaluated for use feelings by the above-described method. The results obtained are shown in Table 7.

EXAMPLE 12

(Cake-Type Foundation)

30 Parts of talc, 5 parts of kaolin, 25 parts of sericite, 10 parts of titanium oxide, 1 part of red iron oxide, 4 parts of yellow iron oxide, 0.1 part of black iron oxide, and 5 parts of silicone resin A-3 prepared in Preparation Example 3 were mixed with a Henschel mixer. This powder mixture was then mixed with 130 parts of hexane and uniformly dispersed therein. The resulting dispersion was treated with a spray dryer to remove the hexane, thereby obtaining a treated powder mixture. This treated powder mixture was introduced into a high-speed blender. Thereto was added a solution prepared by heating a mixture of 5 parts of bees wax, 7 parts of liquid paraffin, 3 parts of tetrakis(3,3,3-trifluoropropyl)tetramethylcyclotetrasiloxane, and 5 parts of silicone resin A-4. The resulting mixture was homogenized, pulverized, and then press-formed into a cake, thereby obtaining a cake-type foundation. This foundation was evaluated for use feelings by the above-described method. The results obtained are shown in Table 7.

COMPARATIVE EXAMPLE 12

A cake-type foundation was obtained in the same manner as in Example 12 except that silicone resin A-3 was omitted in preparing a treated powder mixture and this treated powder mixture was used in an amount of 75.1 parts in place of the treated powder mixture used in Example 12, and that 2 parts of 2-ethylhexyl palmitate and 3 parts of sorbitan sesquioleate were used in place of silicone resin A-4. This foundation was evaluated for use feelings by the above-described method. The results obtained are shown in Table 7.

EXAMPLE 13

(Lipstick)

A mixture having the composition shown below was heated to melt the meltable ingredients and stirred to obtain a uniform mixture. This mixture was further treated with a roll mill to thoroughly disperse the particulate ingredients. Degassing of the resulting mixture was conducted while the molten state thereof was maintained, and the degassed mixture was then poured into a lipstick metal case, thereby obtaining a lipstick. This lipstick was evaluated for use feelings by the above-described method. The results obtained are shown in Table 7.

| Composition: | |
|---|---|
| Paraffin wax | 12 parts |
| Lanolin wax | 10 parts |
| Kaolin | 10 parts |
| Castor oil | 40 parts |
| Octamethylcyclotetrasiloxane | 10 parts |
| Octanoic acid triglyceride | 3 parts |
| Candelilla wax | 3 parts |
| Silicone resin A-1 | 8 parts |
| Titanium oxide | 1 part |
| Red No. 201 | 1 part |
| Red No. 202 | 2 parts |

COMPARATIVE EXAMPLE 13

A lipstick was obtained in the same manner as in Example 13 except that silicone resin B-1 was used in place of silicone resin A-1. This lipstick was evaluated for use feelings by the above-described method. The results obtained are shown in Table 7.

TABLE 7

| | Example | | | Comparative Example | | |
|---|---|---|---|---|---|---|
| | 11 | 12 | 13 | 11 | 12 | 13 |
| Spreadability | ○ | ○ | ○ | x | x | Δ |
| Long-lasting property | ○ | ○ | ○ | Δ | x | Δ |
| Appearance (color) | ○ | ○ | ○ | x | x | ○ |
| Slip property | ○ | ○ | ○ | x | x | Δ |

[Antiperspirants]
Evaluation Method

Antiperspirants to be evaluated were subjected to a sensual test in which five panelists actually used the antiperspirants and evaluated the use feeling thereof.

○: Dry feeling without sticky or stretched feeling
Δ: Slightly sticky or stretched feeling
x: Sticky or stretched feeling with poor lasting property

EXAMPLE 14

(Stick-Type Antiperspirant)

44.8 Parts of decamethylcyclopentasiloxane was mixed with 20.0 parts of stearyl alcohol by stirring. Thereto were then added 5.0 parts of talc, 0.2 part of triclosan, and 20.0 parts of aluminum chloride hydroxide. After this mixture was stirred, 10.0 parts of silicone resin A-1 was added and the resulting mixture was heated to dissolve the soluble ingredients. The resulting mixture was cooled to 50° C. and poured into a case, thereby obtaining a stick-type antiperspirant. This antiperspirant was evaluated for use feeling by the above-described method. The results obtained are shown in Table 8.

COMPARATIVE EXAMPLE 14

A stick-type antiperspirant was obtained in the same manner as in Example 14 except that silicone resin B-2 was used in place of silicone resin A-1. This antiperspirant was evaluated for use feeling by the above-described method. The results obtained are shown in Table 8.

EXAMPLE 15

(Spray-Type Antiperspirant)

Silicone resin A-1 was pulverized with a jet-mill pulverizer to obtain a silicone powder having an average particle diameter of 5 μm. The average particle diameter was measured with a particle size distribution-measuring device (CAPA-500, manufactured by Horiba Seisakusho K.K., Japan). On the other hand, 25.0 parts of isopropyl myristate, 25.0 parts of decamethylcyclopentasiloxane, 0.2 part of triclosan, and 3.8 parts of a perfume were mixed at room temperature to dissolve the soluble ingredients. Thereto were added 23.0 parts of the above-prepared powder of silicone resin A-1 and 23.0 parts of a powder of aluminum chloride hydroxide. The resulting mixture was homogenized to prepare an antiperspirant composition. To 7.0 parts of this composition was added 93.0 parts of LPG as a propellant, thereby obtaining a spray-type antiperspirant. This antiperspirant was evaluated for use feeling by the above-described method. The results obtained are shown in Table 8.

COMPARATIVE EXAMPLE 15

A spray-type antiperspirant was obtained in the same manner as in Example 15 except that talc was used in place of silicone resin A-1. This antiperspirant was evaluated for use feeling by the above-described method. The results obtained are shown in Table 8.

TABLE 8

|  | Example | | Comparative Example | |
|---|---|---|---|---|
|  | 14 | 15 | 14 | 15 |
| Panelist 1 | ○ | ○ | Δ | x |
| Panelist 2 | ○ | ○ | Δ | x |
| Panelist 3 | ○ | ○ | Δ | x |
| Panelist 4 | ○ | ○ | Δ | x |
| Panelist 5 | ○ | ○ | Δ | x |

[Face-Wash Cosmetic Compositions]

Evaluation Method

Face-wash cosmetic composition to be evaluated were subjected to a sensual test in which five panelists actually used the compositions and evaluated for the use feeling thereof. The results obtained are shown as the average of evaluation ratings by the five panelists.

○: Smooth feeling

Δ: Unpleasant feeling x: Painful

Likewise, the compositions were also evaluated for cleansing effect, specifically foundation-removing effect, in a sensual test.

○: Good cleansing effect

Δ: Slightly poor cleansing effect x: Poor cleansing effect

EXAMPLE 16

(Cleansing Cream)

Silicone resin A-4 was pulverized with a jet-mill pulverizer to obtain a silicone powder having an average particle diameter of 5 μm. The average particle diameter was measured with a particle size distribution-measuring device (CAPA-500, manufactured by Horiba Seisakusho K.K.). Subsequently, 2.0 parts of this powder of silicone resin A-4, 3.0 parts of spherical methylpolysilsesquioxane-resin fine particles (average particle diameter: 0.5 μm), 10 parts of solid paraffin, 3 parts of bees wax, 15 parts of vaseline, 41 parts of liquid paraffin, 4.2 parts of sorbitan sesquiisostearate, and 0.8 part of poly(oxyethylene(20)) sorbitan monooleate were mixed with heating to melt the meltable ingredients. Thereto was added dropwise 20.5 parts of hot water having a temperature of 70° C. The resulting mixture was stirred and cooled to 40° C., thereby obtaining a cleansing cream. This cream was evaluated for use feeling and cleansing effect by the above-described method. The results obtained are shown in Table 9.

COMPARATIVE EXAMPLE 16

A cleansing cream was obtained in the same manner as in Example 16 except that 5.0 parts of a polyethylene powder (average particle diameter 150 μm) was used in place of 2.0 parts of the powder of silicone resin A-4 and 3.0 parts of the spherical methylpolysilsesquioxane-resin fine particles (average particle diameter 0.5 μm). This cream was evaluated for use feeling and cleansing effect by the above-described method. The results obtained are shown in Table 9.

TABLE 9

|  | Example 16 | Comparative Example 16 |
|---|---|---|
| Use feeing | ○ | Δ |
| Cleansing effect | ○ | ○ |

While the invention has been described in detail and with reference to specific embodiments thereof, it will be apparent to one skilled in the art that various changes and modifications can be made therein without departing from the spirit and scope thereof.

What is claimed is:

1. A cosmetic composition comprising a silicone resin consisting of from 80 to 95 mol % of $R^1Si(O)_{1.5}$ units and from 5 to 20 mol % of $(R^2)_3Si(O)_{0.5}$ units, wherein the sum of the $R^1Si(O)_{1.5}$ units and the $(R^2)_3Si(O)_{0.5}$ units is 100 mol %, and wherein the amount of residual silanol groups in said resin is 0.5 wt % or less, wherein $R^1$ and $R^2$, which are the same or different, each represents a methyl group, an ethyl group, a propyl group, a butyl group, a vinyl group, a phenyl group, or a 3,3,3-trifluoropropyl group; and wherein said resin is present in an amount of 0.1 to 45% by weight based on the weight of the cosmetic composition.

2. A cosmetic composition as claimed in claim 1, wherein said silicone resin is obtained by reacting (A) 100 parts by weight of a silanol group-containing organopolysilesquioxane comprising $R^1Si(O)_{1.5}$ units with (B) from 5 to 100 parts by weight of a silicone compound represented by $(R^2_3Si)_aZ$ wherein a is an integer of 1 or 2, and when a is 1, Z represents hydrogen atom, hydroxyl group, or a hydrolyzable group and when a is 2, Z represents —O—, —N(X)—, or —S—, wherein X represents a hydrogen atom, a monovalent hydrocarbon group having from 1 to 4 carbon atoms, or $(R^2)_3Si$—, wherein $R^1$ and $R^2$, which are the same or different, each represents a methyl group, an ethyl group, a propyl group, a butyl group, a vinyl group, a phenyl group, or a 3,3,3-trifluoropropyl group.

3. A cosmetic composition as claimed in claim 2, wherein the organopolysilsesquioxane contains from 1 to 10% of the silanol group.

4. A cosmetic composition as claimed in claim 3, wherein the silanol group content is 1 to 5 wt %.

5. A cosmetic composition as claimed in claim 2, wherein the hydrolyzable group is an alkoxy group, an alkenyloxy group, an acyloxy group, an organooxime group, an organoaminoxy group, an organoamino group, or an organoamido group.

6. A cosmetic composition as claimed in claim 1, wherein said organopolysilsesquioxane, ingredient (A), has a molecular weight of at least 1,000.

7. A cosmetic composition as claimed in claim 1, wherein said silicone resin has a softening point of at least 50° C.

* * * * *